(12) United States Patent
Dimas et al.

(10) Patent No.: US 7,016,566 B2
(45) Date of Patent: Mar. 21, 2006

(54) LIGHTGUIDES

(75) Inventors: Chris Fotis Dimas, Toronto (CA); John Joseph Kuta, Oakville (CA)

(73) Assignee: EXFO Photonics Solutions Inc., Mississauga (CA)

( * ) Notice: Subject to any disclaimer, the term of this patent is extended or adjusted under 35 U.S.C. 154(b) by 0 days.

(21) Appl. No.: 10/766,831

(22) Filed: Jan. 30, 2004

(65) Prior Publication Data

US 2005/0169575 A1      Aug. 4, 2005

(51) Int. Cl.
G02B 6/32       (2006.01)
G02B 6/20       (2006.01)

(52) U.S. Cl. .......................... 385/35; 385/33; 385/125

(58) Field of Classification Search ................ 385/31, 385/33, 35, 102, 125
See application file for complete search history.

(56) References Cited

U.S. PATENT DOCUMENTS

| | | | |
|---|---|---|---|
| 3,740,113 A | 6/1973 | Cass | |
| 3,995,934 A | 12/1976 | Nath | |
| 4,045,119 A | 8/1977 | Eastgate | |
| 4,235,508 A | 11/1980 | Kaprelian | |
| 4,697,870 A | 10/1987 | Richards | |
| 4,927,231 A | 5/1990 | Levatter | |
| 5,452,395 A | 9/1995 | Schichman et al. | |
| 5,608,834 A | 3/1997 | Van Leeuwen | |
| 5,684,908 A | 11/1997 | Kross et al. | |
| 5,717,807 A | 2/1998 | Theroux et al. | |
| 5,857,052 A * | 1/1999 | Nath | 385/125 |
| 5,896,483 A * | 4/1999 | Wojcik et al. | 385/125 |
| 6,016,372 A * | 1/2000 | Fein et al. | 385/12 |
| 6,163,641 A * | 12/2000 | Eastgate | 385/125 |
| 6,418,257 B1 * | 7/2002 | Nath | 385/125 |
| 6,813,427 B1 * | 11/2004 | Kaltenbacher et al. | 385/125 |

OTHER PUBLICATIONS

Optical System Design, chapter 5, pp. 78-85.
W.J. Cassarly, editor: M. Bass, Handbook of Optics, vol. 3, Second Edition, McGraw-Hill, 2001, chapter 2, pp. 2.25-2.33.

* cited by examiner

Primary Examiner—John D. Lee
Assistant Examiner—Rhonda S. Peace
(74) Attorney, Agent, or Firm—Thomas Adams

(57) ABSTRACT

In a light delivery system comprising a lightguide coupled to an optical apparatus for delivering substantially uniform light to a predetermined plane within the apparatus, images of non-uniformities caused by imperfections at or near an outlet end of the lightguide are displaced away from the predetermined plane. The image displacement may be performed by a lens adjacent the end of the lightguide, or integral therewith, or by a suitably formed plug or end cap of a liquid lightguide.

40 Claims, 9 Drawing Sheets

Bright regions (source)

Dark regions (seal)

LIGHTGUIDES

BACKGROUND OF THE INVENTION

1. Technical Field

The invention relates to lightguides, and is especially, but not exclusively, applicable to liquid and fiberbundle lightguides for transmitting ultraviolet light. The invention also relates to optical apparatus with such a lightguide coupled thereto, and to adapters for coupling them.

2. Background Art

Liquid and fiberbundle lightguides are typically used in applications where a large amount of radiation (typically UV, visible or IR) must be delivered to a remote location. Much of the art relating to the use of liquid lightguides for UV light transmission is directed to the curing of industrial photo-curable adhesives. This is because these applications require the application of intense ultraviolet or blue light to the chemicals being treated.

Liquid lightguides also have been employed with remote light sources for imaging applications, such as microscopy. In such an application, light from the guide usually is collimated or concentrated prior to illuminating a sample placed in the objective field conjugate of the microscope. In the case of a fluorescent microscope, the illumination of the sample by UV light allows for the visualization of molecules that are capable of fluorescing.

A typical liquid lightguide is composed of a core containing a highly transmissive liquid surrounded by a sheath that is generally made of a material having a low refractive index, such as Teflon™. Total internal reflection of the light occurs at the boundary between the liquid and the surrounding sheath. Transparent sealing members, such as glass rods, are placed at both ends of the guide to make a liquid-tight seal.

Many applications of lightguides require a very uniform irradiation distribution. This requirement is especially onerous where lightguides are used for imaging applications requiring a very uniform irradiation distribution across the field of view of the objectives. The present inventors have discovered that one reason why this has been difficult to achieve in practice is the presence of virtual images that are produced by the guide. In the case of liquid lightguides, the images arise from light scattering that occurs due to non-uniformities, such as any imperfections at the sheath, the sealing member, or at the interface between the liquid and the sealing member.

For example, at the interface between the liquid and the sealing member, air gaps are created by an uneven wetting of the liquid at the interface. The result is the creation of a number of mirror-like images along the transverse plane coincident with the sealing member. As this virtual source plane is imaged at a finite distance from the lenses, the outcome is a non-uniform irradiance distribution across the objectives of the microscope. Such images are well documented for sealing members, usually known as integrating or mixing rods, in the form of rods having straight edged cross-sections such as squares and hexagons, (see W. J. Cassarly, *Handbook of Optics Vol. 3*, Second Edition, Ch. 2, p. 2.28–2.33, McGraw-Hill, 2001, editor M. Bass), but the same effect applies to cylindrical rods, which are commonly used to seal the ends of tubular liquid lightguides.

Fiberbundle lightguides made of some type of glass or quartz material also are used for imaging applications, and they also exhibit undesirable non-uniformities which scatter light and can be imaged onto the image conjugate plane of the imaging system. In the specific case of fused fiberbundles, for which the individual fibers at the distal end of the lightguide have been mechanically fused together, the non-uniformities can be due, for example, to the contact region between the end of the fused bundle and a quartz rod, or to irregularities or inhomogeneity in or at the fused region of the bundle.

It is known to obtain a more uniform irradiance distribution by placing a diffuser at the end of a liquid lightguide. U.S. Pat. No. 5,684,908 discloses a system for photocuring of chemicals in which such a diffuser changes the shape of the light beam such that the majority of the beam is of a uniform intensity. A drawback to the use of such diffusers, however, is that the resulting optical coupling efficiency to the object to be illuminated, for example, a sample in a microscope, is less than optimal.

SUMMARY OF THE INVENTION

The present invention seeks to eliminate, or at least mitigate, the disadvantages of the prior art, or at least provide an alternative. To this end, in embodiments of the present invention, images produced by non-uniformities at the outlet ends of the lightguides, for example those at the interface between the liquid and the sealing member in a liquid lightguide, are displaced away from the plane at which the uniform light is required.

This plane, henceforth the predetermined plane of the apparatus, may be the objective field conjugate of a microscope or, in curing apparatus, a plane at or adjacent a surface to be irradiated.

According to a first aspect of the invention, there is provided optical apparatus and a light delivery system for supplying said light to an input port of the apparatus such that the light illuminates a predetermined image plane within the apparatus, said light delivery system comprising a lightguide for conveying said light from a light source unit to said input port, the lightguide having an inlet end for connection to an output port of the light source unit and an outlet end for coupling to the input port of the apparatus so as to provide substantially uniform light at said predetermined image plane, there being imaging means at or adjacent the outlet end of the lightguide for imaging said outlet end of said lightguide at said predetermined image plane and imaging non-uniformities present at or adjacent the outlet end of the lightguide away from said predetermined image plane.

A light delivery system for supplying light to an input port of an optical apparatus such that the light illuminates a predetermined image plane within the apparatus, said light delivery system comprising a light source unit for supplying said light, a lightguide for conveying said light from the light source unit to said input port; the lightguide having an inlet end connected to an output port of the light source unit and an outlet end coupled to the input port of the apparatus so as to provide substantially uniform light at said predetermined image plane, there being imaging means at or adjacent the outlet end of the lightguide for imaging said outlet end of said lightguide at said predetermined image plane and imaging non-uniformities present at or adjacent the outlet end of the lightguide away from said predetermined image plane.

According to a third aspect of the invention, there is provided a lightguide for connecting a light source unit to an optical apparatus, so as to supply light to an input port of the apparatus that illuminates a predetermined image plane within the apparatus, the lightguide having an inlet end for connection to the output port of a light source unit and an outlet end for connection to the input port of the apparatus, there being imaging means at or adjacent the outlet end of the lightguide for imaging said outlet end of said lightguide at said predetermined image plane and of imaging non-uniformities present at or adjacent the outlet end of the lightguide away from said predetermined image plane.

In embodiments of any of the foregoing aspects of the invention, the lightguide may comprise a liquid lightguide or a fiberbundle lightguide. An adapter comprising, for example, collector lenses, may be provided to couple the lightguide to an input port of the apparatus. Where the displacing means is a separate lens, it could be provided in the adapter.

An adapter unit for interfacing light from a lightguide of a light delivery system to an input port of the optical apparatus having a predetermined image plane within the apparatus such that the light illuminates said predetermined image plane, the adaptor having an output port for connection to said optical apparatus and an input port for connection to the outlet end of the lightguide and comprising optical elements for providing substantially uniform light at said predetermined image plane, there being means at or adjacent the input port of the adaptor for imaging said outlet end of said lightguide at said predetermined image plane and imaging non-uniformities present at or adjacent the outlet end of the lightguide away from said predetermined image plane.

In preferred embodiments of the different aspects of the invention, the means for displacing of the image of the non-uniformities of the lightguide away from the image of the outer end face may comprise a positive or negative lens placed in the adapter means at the outlet end of the lightguide. Alternatively, the displacing means may comprise part of the lightguide itself, for example, as a positive or negative lens formed integrally with the end of the sealing member.

Alternatively, for a liquid lightguide, the displacing means may comprise a sealing member of a hollow construction, in which case the required displacement occurs because the interface is placed closer to the terminus of the outlet end.

The foregoing and other objects, features, aspects and advantages of the present invention will become more apparent from the following detailed description, in conjunction with the accompanying drawings, of a preferred embodiments of the invention which are described by way of example only.

DESCRIPTION OF THE PREFERRED EMBODIMENTS

Figure 1:
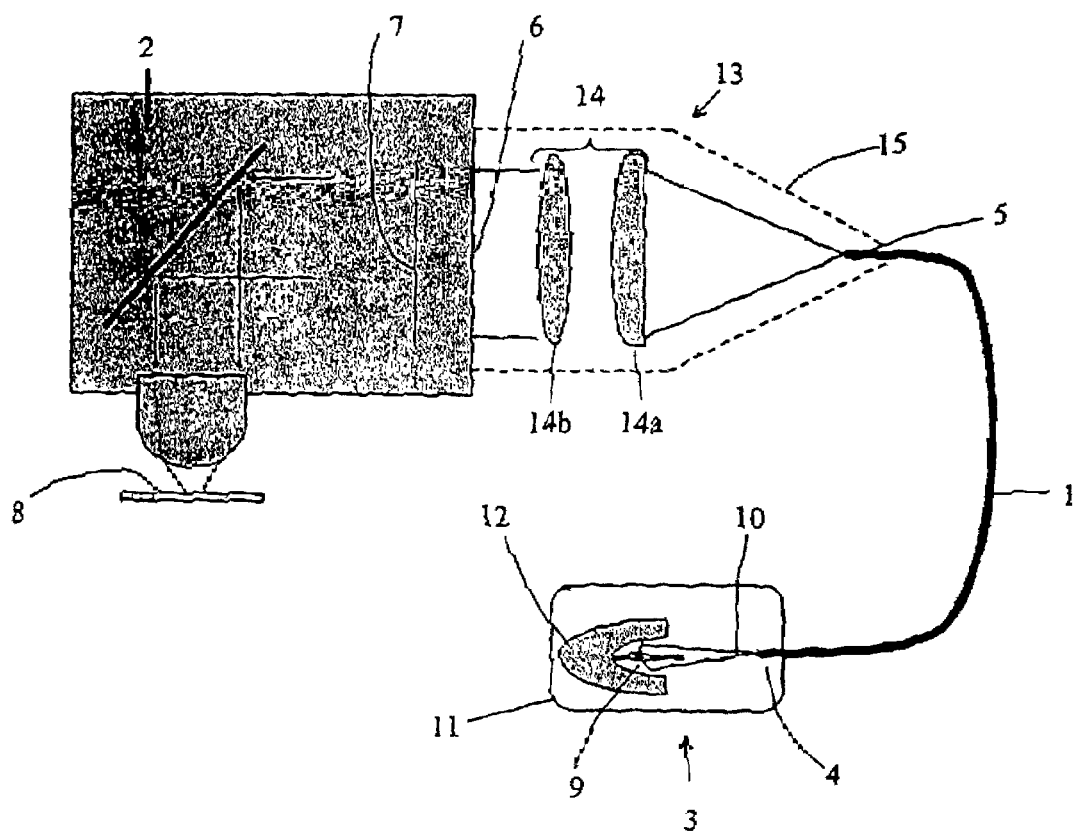
FIG. 1 is a diagram of a conventional remote illuminator arrangement for fluorescence microscopy employing a known liquid lightguide.

FIG. 1 illustrates a lightguide 1 coupling a microscope 2, for example a fluorescent microscope, to a remote illuminator, i.e., light source unit 3. Light from light source unit 3 is transmitted through the inlet end 4 of the lightguide 1 and exits through an outlet end 5 to supply light to an input port 6 of the microscope. Light from the input port 6 then passes through the microscope to the microscope's objective field conjugate 7 and is focused before illuminating a sample placed at the objective plane 8 of the microscope 2. The position of the objective field conjugate 7 varies depending on the configuration of the microscope.

The light source unit 3 comprises a light source 9, which is typically a UV lamp. The lightguide 1 has an inlet end 4 coupled to an output port 10 in a housing 11 of the light source unit 3 so that its end face is at a focus of an ellipsoidal reflector 12, which focuses the light from the light source 9 onto the inlet end 4 of the lightguide 1.

The outlet end 5 of the lightguide 1 is coupled to the input port 6 of the microscope 2 by an adapter unit 13, which comprises collector optics 14, specifically a plano-convex spherical lens 14a and a bi-convex spherical lens 14b in a housing 15. The outlet end 5 of the lightguide is attached at one end of the housing 15 at the focal plane of the collector optics 14. The opposite end of the housing 15 is attached to the microscope port 6 and interfaces the collector optics 14 to the microscope's internal collector optics (not shown).

Figure 2A:
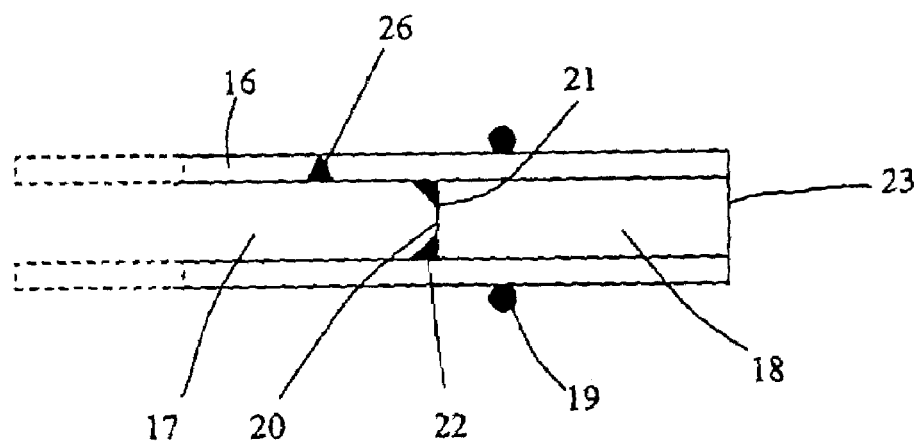
FIG. 2a is a schematic drawing showing the structure of an end portion of the known liquid lightguide.

The physical structure of one end of a conventional liquid lightguide is shown in FIG. 2a. In conventional lightguides, both ends are identical. Accordingly, and since only the outlet end is of particular interest in the context of the present invention, only outlet end 5 of the lightguide will be described.

Thus, the sheath 16 of the guide contains a light transmissive liquid 17, for example polydimethylsiloxane. Total internal reflection of light passing through the guide occurs at the boundary between the liquid and the sheath, as a result of the sheath having a significantly lower refractive index than that of the transmissive liquid. Typically, the sheath 16 is made of polytetrafluoroethylene (e.g. Teflon™).

A light-transmissive sealing member, specifically a short glass rod plug 18, inserted into the end of the sheath 16, plugs or seals that end of the lightguide 1 to contain the transmissive liquid 17 within the sheath 16. The sealing function is critical to the integrity and reliability of the lightguide so reinforcement of the sealing function may be enhanced by means of a pressure gasket, such as an O-ring 19, around the exterior of the portion of sheath 16 that surrounds the glass plug 18 to clamp the sheath to the glass rod plug 18. A faulty seal could result in the formation of air bubbles, which would scatter the light from the guide and render it useless.

In the region of the outlet end containing sealing plug 18, a virtual source plane is created which produces a number of mirror-like virtual sources along a transverse plane coincident with the sealing member. The source plane arises due to a liquid/sealing plug interface 20 between the inner end surface 21 of plug 18 and the liquid contained in the sheath 16. At the interface 20, an air-gap 22, shown in FIG. 2a, is created due to the high surface tension of the liquid. Due to the presence of the air-gap 22, light that passes through the interface 20 scatters from this region and produces a visible black ring (for a sealing plug 18 with a circular cross-section).

Figure 3A:
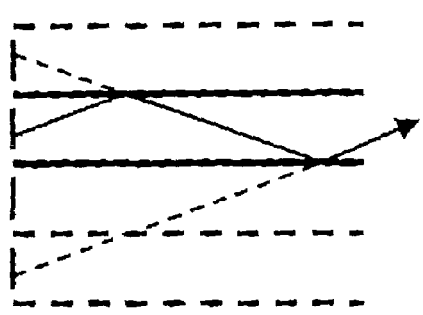
FIG. 3a is a diagram depicting the formation of a virtual source plane due to multiple reflections in a glass rod sealing the output end of the lightguide.
Figure 3B:
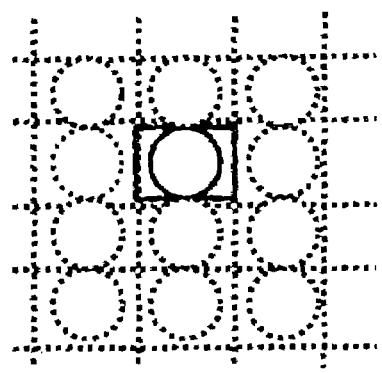
FIG. 3b is a diagram showing the virtual source plane produced when the glass rod is of rectangular cross-section.
Figure 3C:
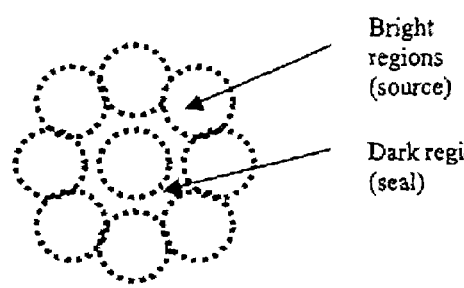
FIG. 3c is a diagram showing the virtual source plane produced when the glass rod is of circular cross-section.

This effect is shown in FIG. 3a, which depicts light scattering in a glass rod plug as lines emanating from the interface. The resulting virtual source plane created by sealing members of circular and rectangular cross sections are shown in FIGS. 3b and 3c, respectively. When a sealing plug 18 of circular cross-section is employed, an infinite and continuous number of normals to the tangents of the circle are present (FIG. 3c). This produces a virtual source plane located at the inner end surface of the sealing member, which consists of a number of dark concentric rings.

Other sources of non-uniformity for liquid lightguides, depicted in FIG. 2a, include the imprint caused by the pressure gasket 19 squeezing onto the sheath and the glass rod plug, and physical imperfections on the Teflon™ sheath 16 and the glass rod plug 18 themselves, causing scattering of light at those regions.

Figure 4:
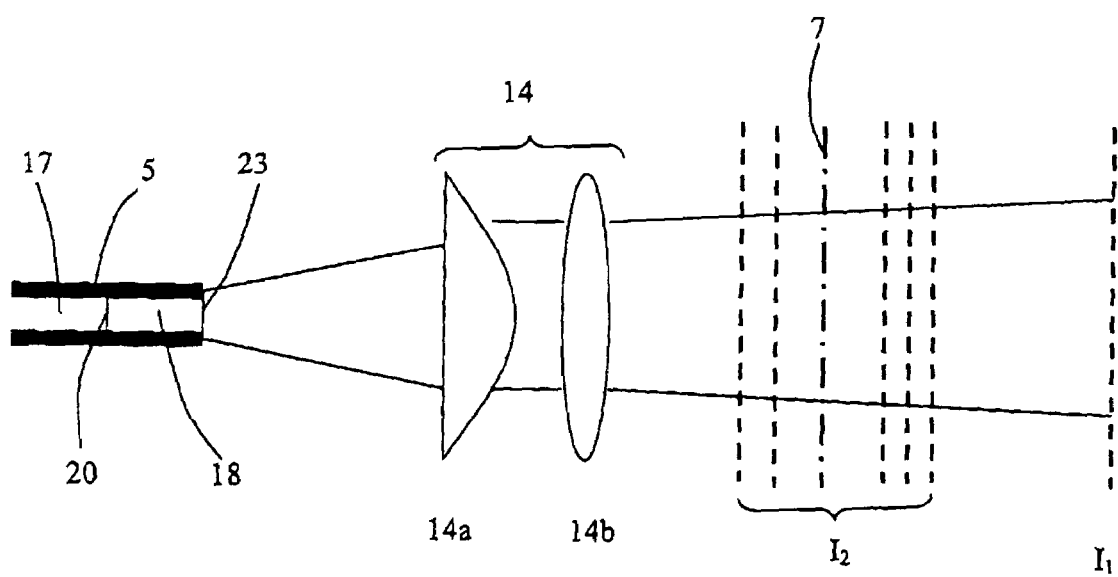
FIG. 4 is a schematic diagram illustrating an arrangement of an output end of a liquid lightguide coupled by an adapter means comprising collector lenses to illuminate the objective field conjugate (OFC) of an optical apparatus.

Images formed by the interface between the liquid and the rod of a liquid lightguide will be discussed in the context of the specific example of a liquid lightguide being used to illuminate a microscope as in FIG. 1. When the light from the lightguide 1 passes through the collector lens means 14, the light from the outer end face 23 is "imaged" at infinity, or at least far from the optical field conjugate, but the virtual source plane is imaged at a finite distance from the collector lens, FIG. 4 illustrates the effect of such image formation in the microscope arrangement of FIG. 1. FIG. 4 depicts the outlet end 5 of the lightguide 1 projecting light onto the collector lens means 14 to produce substantially collimated light. The continuum of the images produced by the virtual source plane is shown as $I_2$. Because the images are located in the vicinity of the objective field conjugate (OFC), the outcome is that light of a non-uniform irradiance is projected across the OFC of the microscope. The image of the outer endface 23 of the sealing plug 18, shown as $I_1$, is much further away from the OFC.

Figure 3D:
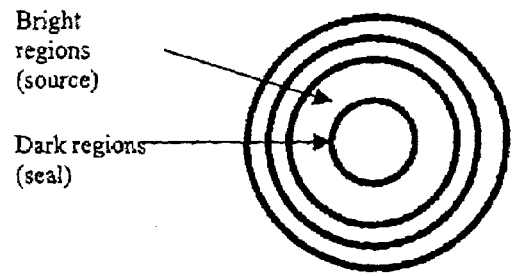
FIG. 3d is a diagram showing the image of the virtual source plane created by collector optics.

FIG. 3d shows an end-on view of the image of the virtual source plane created by the lens means 14. Due to the formation of a virtual source plane containing a continuous number of normals to the tangent of the circle, a virtual image of concentric circles is created. This is shown as bright regions and dark regions corresponding to the images of the air-gap 22 and other sources of scattering such as the pressure gasket 19.

Referring again to FIG. 4, the images $I_2$ comprise a continuum of dark rings $I_2$ formed over a range of distances from the collector lens means 14. This effect is due to spherical aberrations in the collector lenses 14, which makes images from the largest rings at the edges of the virtual source plane form at a closer distance to the collector lenses 14 than the smaller rings located nearer the centre of the virtual source plane.

Figure 5:
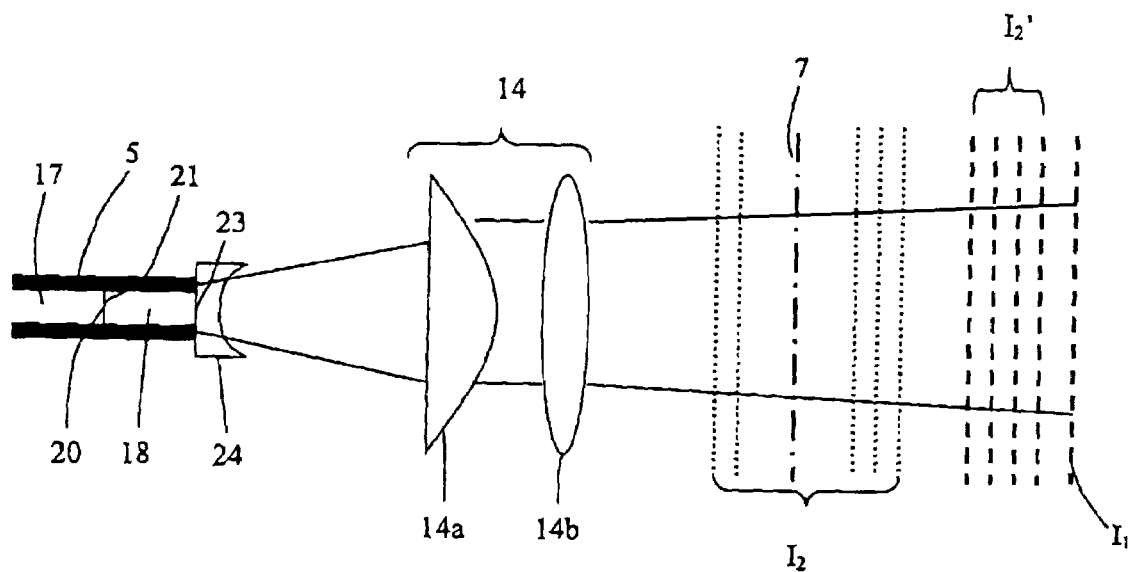
FIG. 5 is a schematic diagram illustrating the use of a negative lens positioned adjacent the output end of a lightguide for displacing images away from the OFC in accordance with a first embodiment of the present invention.

FIG. 5 illustrates a first embodiment of the invention, which is identical to the known system shown in FIG. 4, except for the addition of a means 24, specifically a lens, adjacent the outlet end 5 of the lightguide 1 for displacing the images of the liquid/sealing plug interface 20. The images of the interface 20 before and after displacement are shown in FIG. 5 as $I_2$ and $I_2'$ respectively. As can be seen in FIG. 5, the lens 24 displaces the image of the interface 20 further from the collector lens means 14. Because the image $I_2'$ is shifted well beyond the OFC, it does not affect the distribution of light and a uniform irradiance of light across the OFC is achieved.

Although not intending to be bound by theory, it is postulated that the image of the virtual source plane is shifted due to the combined effect of the negative lens 24 and the collector lens means 14. One can think of this as the negative lens 24 bringing the liquid sealing plug interface 20 closer to the collector lens means 14, or as the negative lens 24 and collector lens means 14 working together to create a weaker lens set with a smaller effective focal length, which thereby pushes the image of the liquid/sealing plug interface 20 further from the lenses 14. When thought of in the former sense, the negative lens 24 changes the effective position of the interface 20 by an amount equal to its effective focal length. In any case, the position of the image of the virtual source plane is moved further away from the lenses 14, well beyond the position of the OFC.

While the position of the image $I_2$ of the virtual source plane is moved, the position of the image of the outlet end 5 of the lightguide 1 should be maintained substantially at infinity. This is shown in FIG. 5, where the position of the image $I_1$ substantially at infinity and the field of the beam of the outlet end 5 are maintained while the image is shifted. This results because, when the lens 24 is placed at the conjugate plane of the outlet end 5, the height of the marginal rays on the lens 24 is low.

A particular example of such an optical configuration could consist of a glass rod 18 having length equal to 30 mm, and the collector optics having effective focal length (EFL) equal to 50 mm. In this case, the image of the liquid/sealing plug interface 20 will appear in the region of 13 cm away from the collector lens 14. With the addition of a negative lens 24 with EFL equal to −18 mm, the image of the interface 20 will be displaced away from the collector lenses 14 by approximately an additional 13 cm; hence it will be positioned 26 cm from the collector lens 14.

In imaging applications where the OFC is positioned at a large distance from the collector lenses 14, for example 25 cm, it may be desirable to use a positive lens instead of negative lens 24. Such a positive lens will place the virtual images closer to the collector lenses 14. As with the negative lens 24, because it is substantially at the conjugate plane of the outlet end 5, the positive lens will not change the field of the collimated beam, or the position of the image of lightguide endface, to any significant extent, but will move the image created by liquid/seal interface 20 at the inner end of the sealing member in relation to the image of the endface 5.

It is envisaged that the positive or negative lens 24 could be integrated into the end of the lightguide 1. More particularly, the curvature of the outlet end 5 of the sealing plug 18 could be varied to form a lens, thereby avoiding the use of the separate positive or negative lenses altogether.

It will be appreciated that the positive and negative lenses have the same effect as displacing the interface 20 away from the outer end of the second sealing plug 18. It would be possible, therefore, to dispense with the positive or negative lens 24 and configure the sealing plug 18 so that its opposite end surfaces are very close together, at least as compared with those of known lightguides, so that both both end surfaces are substantially at the image conjugate plane of the collector optics. Embodiments of the invention employing this approach will be described with reference to FIGS. 6 and 7.

Figure 6:
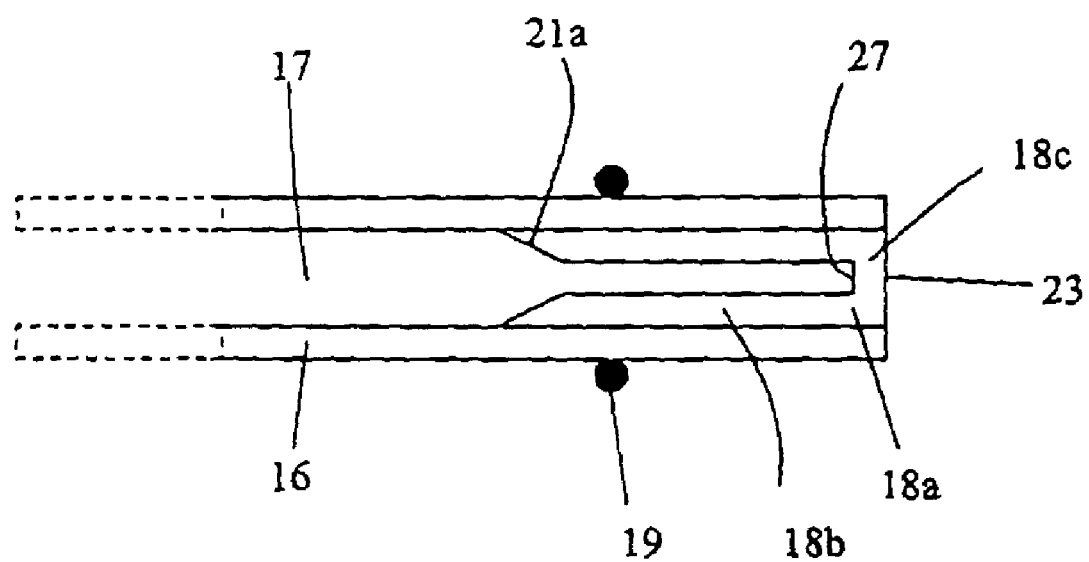
FIG. 6 is a diagram depicting an end portion of a liquid lightguide with a hollow glass rod positioned within the inner wall of the sheath in accordance with a second embodiment of the invention.
Figure 7:
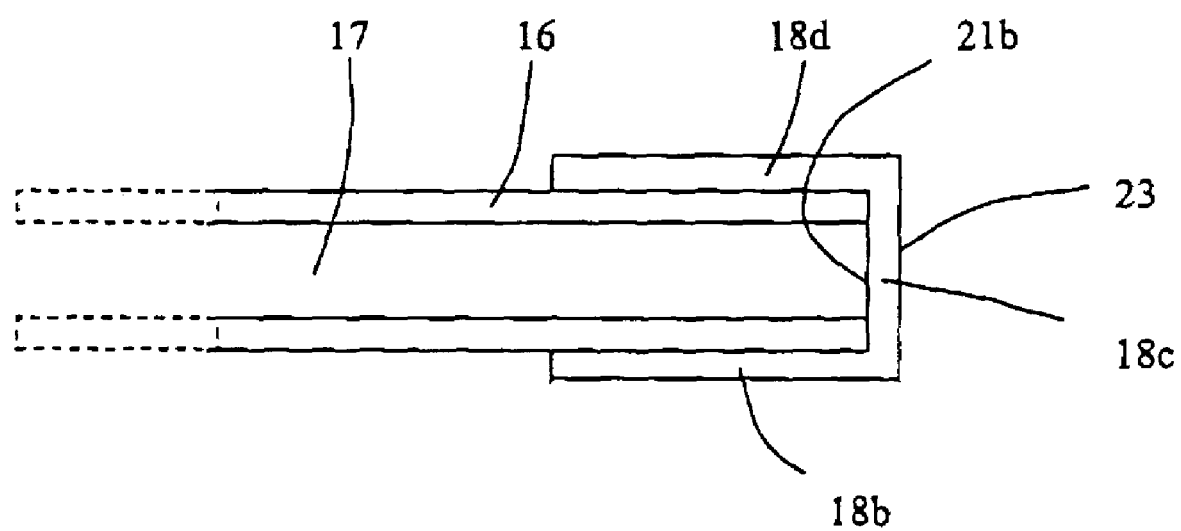
FIG. 7 is a diagram of a liquid lightguide with a hollow glass rod positioned around the external surface of the sheath in accordance with another embodiment of the present invention.

FIGS. 6 and 7 illustrate embodiments of the invention in which the sealing plug 18, at least the one at the outlet end, is of a hollow construction so that interface 20 between the sealing plug 18 and the liquid 17, at least that part (21b) of the interface through which the light passes, is in close proximity to the outlet end 5 of the lightguide 1, thereby placing the images of the virtual source plane beyond the collector lenses 14. By way of example, if the interface 20, i.e., the inner end surface of sealing plug 18, is situated 2–3 mm from the outlet end face 5 of the guide 1, the images of the interface 20 can be moved to at least 1 m well away from the collector lenses 14.

FIG. 6 shows a hollow sealing plug 18a in the form of a hollow glass rod dimensioned such that the sheath 16 fits tightly around its exterior cylindrical surface. A regular pressure gasket, such as the O-ring 19, is used to reinforce the seal between the sheath 16 and the rod plug 18a.

The internal annular end surface 21a of the tubular portion 18b of glass rod 18a interfaced with the liquid 17 preferably is beveled in order to produce a surface that can be wetted. The tubular portion 18b is closed at its outer end by end wall 18c, the outer surface of which is endface 23 of the lightguide and the inner surface of which is the above-mentioned part 21b of the interface 21 through which the light passes. End wall 18c is so thin that the images of its internal and external surfaces are well away from the predetermined plane (objective field conjugate).

FIG. 7 shows an alternative hollow sealing member 18d in the form of a hollow cylinder similar to sealing member 18a but which fits onto the exterior of the outer wall of the sheath 16 like an end cap, and does not have beveled annular end surfaces. In this case, a mechanical mechanism, adhesive, or delayed expansion of the material making up the sheath 16 may be used to adhere the exterior of the sheath 16 to the interior of the sealing member 18d.

The sealing plug may also be constructed of blown glass and its end wall 18c resemble the bottom of a test-tube. It should be noted, however, that a sealing member formed in this manner should not be used in applications where the end cannot have an optical power (cannot be curved).

Figure 2B:
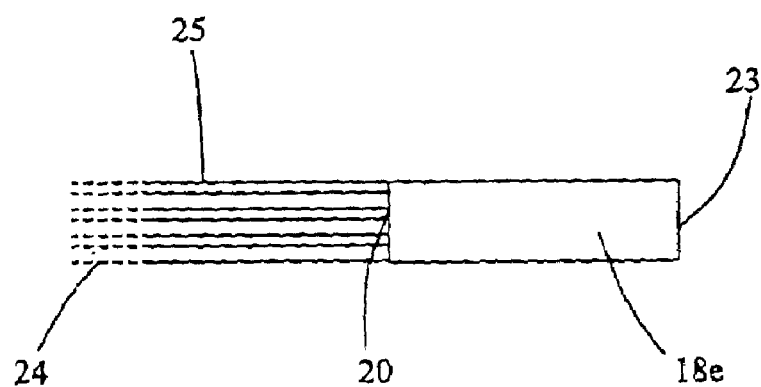
FIG. 2b is a schematic drawing showing the structure of an end portion of a known fused fiberbundle lightguide.

It will be appreciated that other kinds of lightguides may manifest similar sources of non-uniformity, as illustrated, for example, in FIG. 2b, which shows one end of a fiberbundle lightguide. Conventional fiberbundle lightguides do not have fused ends and therefore, for most fiberbundle lightguides, the end of the non-fused region would be the output end of the lightguide. In many cases where maximum power coupling is of great importance, the end of the fiberbundle is fused to create a fused portion having a higher packing fraction. In the particular fiberbundle lightguide shown in FIG. 2b, the end portions of the fiberbundle 24 are fused together to form a fused portion 25 having an increased packing fraction. The distal end of the fused portion 25 is attached to a rod 18, of glass, quartz or other suitable material, which manipulates the intensity distribution of the light leaving the light guide.

Fusing the fiber allows for greater coupling efficiency to the collector optics 14 and the collector optics of the optical apparatus (not shown) since the total power through the lightguide remains the same but the spatial density is increased, In other words, the etendue (the product of the area and the solid angle of a light source) of the light emitted from the fiberbundle is decreased.

Furthermore, in FIG. 2b, the glass or quartz rod 18e does not seal liquid, as in the liquid lightguide, but is used for changing the near field intensity distribution of the light in order to mimic, for example, what it would be if a liquid lightguide were used. Also, the rod 18e provides the added benefit of structural stability.

In the fiberbundle lightguide of FIG. 2b, sources of non-uniformities or light scattering centers include imperfections in the glass rod 18, imperfections at the interface 20 between the rod 18 and the fused portion 25, imperfections at the transition between fused portion 25 and the fiberbundle 24, and imperfections within the fused portion 25. These are only a few examples and not meant to be inclusive of all scattering centers present within a fiberbundle of the kind shown in FIG. 2b or any other variation of a fiberbundle to be developed in the future.

It will be appreciated by those skilled in this art that certain of the specific means described above for displacing images created in a liquid lightguide may also be utilized in a fiberbundle lightguide to displace the images created by such non-uniformities.

Figure 8A:
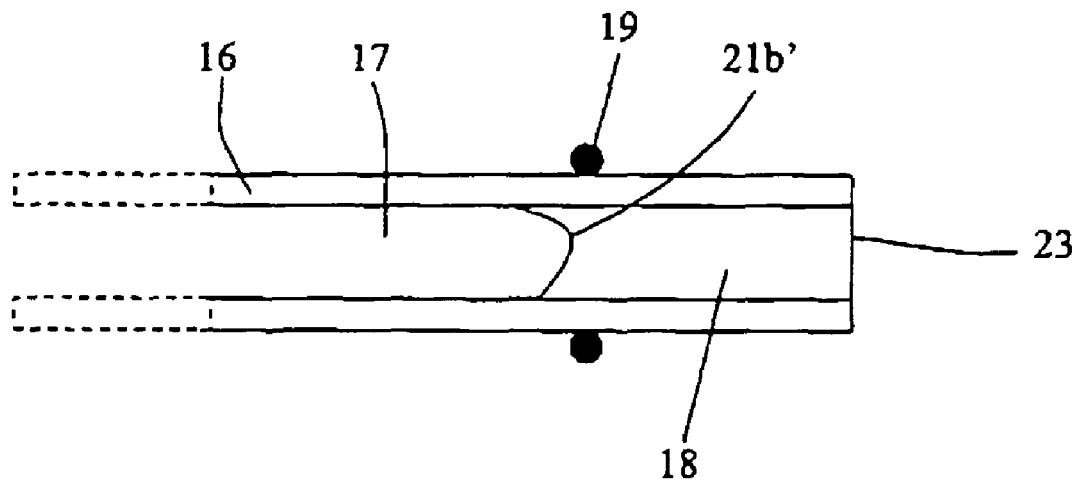
FIG. 8(a) is a diagram of a liquid lightguide where the inner end of the glass rod is of a concave curvature that is smooth.
Figure 8B:
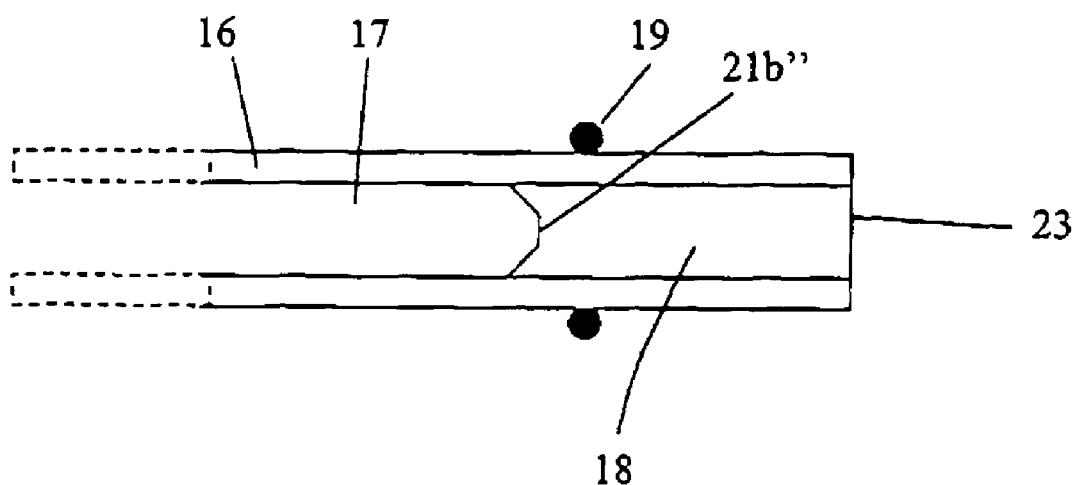
FIG. 8(b) is a diagram of a liquid lightguide where the inner end of the glass rod is of a concave curvature that is facetted.

Modifications to the above-described liquid lightguide embodiment of FIG. 5 are shown in FIGS. 8(a), and 8(b), respectively. In FIGS. 8a and 8b, the inner end surfaces 21b' and 21b'', respectively, of glass rod 18 are each curved to enhance wetting of the surface thereby reducing air-gap formation. The curvature of the surface may be smooth as depicted in FIG. 8a or facetted as depicted in FIG. 8(b).

Figure 9:
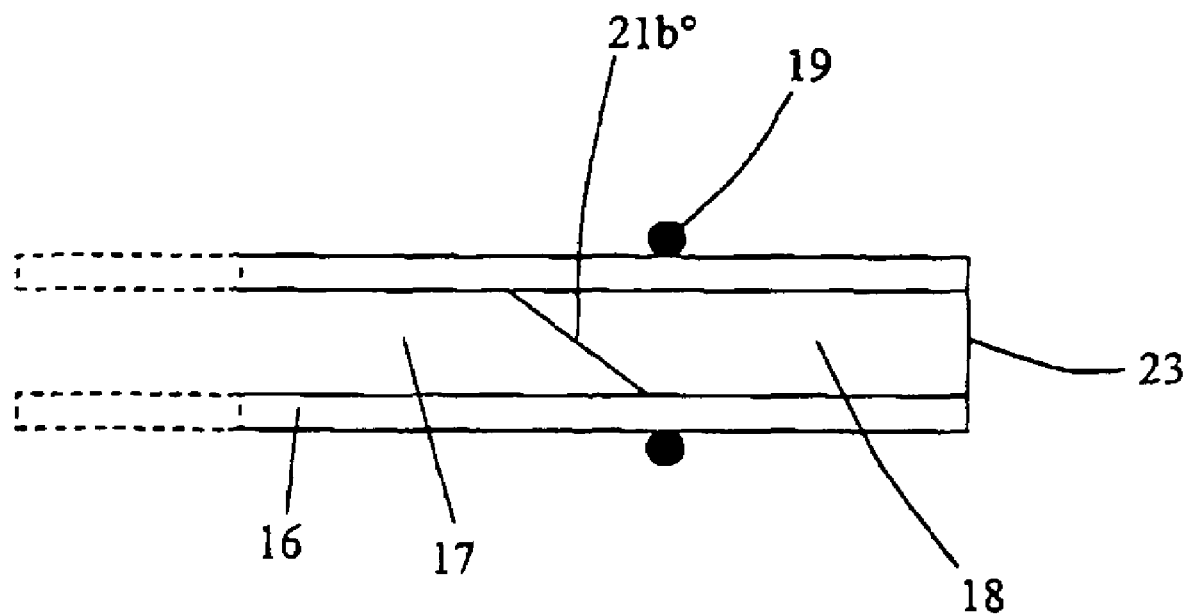
FIG. 9 is a diagram of a lightguide where the inner end of the glass rod is cut at an angle.

FIG. 9 shows an alternative embodiment of liquid lightguide in which the inner end surface $21b°$ of the sealing plug 18 is inclined at an angle of about 45 degrees to the plane perpendicular to the longitudinal axis of the sealing plug 18, which has the effect of spreading out the virtual source plane in object space. The result is that the images of the interface $21b°$ are also spread out and a sort of smeared dot-pattern or spiral ring pattern emerges as a function of distance from the collector lens means. It should be noted, however, that low quality collimator lenses 14 could produce a continuum of images due to spherical aberrations. This may transform the dark dots into hemi-rings or circular rings, which is not an ideal situation. Furthermore, a large air-gap could be produced at the portion of the interface where the angle between the interface and the inner wall of the sheath is the smallest.

Generally, the adapter optics will be customized for the microscope or other apparatus with which the lightguide is to interface. The collector adapter optics 14 may be designed by first testing a lens set consisting of two lenses, which together have a small focal length and a small f-number (f/#=½NA). Such a combination of lenses should ensure that all of the light exiting the guide is collected by the adapter optics. This is important in order to maximize the power coupling efficiency. However, power maximum coupling efficiency is not achieved if the exit pupil of the collector lenses 14 is larger than the entrance pupil of the input port 6. Because the lenses are of small focal length, they will be strong and will therefore tend to exhibit a high amount of spherical aberration. This could result in the size of the exit pupil being too large. If the exit pupil size is larger than the entrance pupil size, it may be reduced by selecting collector lenses 14 with a longer focal length and a larger f-number. Collector lenses of differing focal lengths and f-numbers may be tested until a desired coupling efficiency is achieved.

Table I below describes, by way of example, adapter optics and displacing lens which are suitable for use with a model #TE2000 microscopes made by Nikon:

TABLE I

| Surface | Radius (mm) | Thickness (mm) | Substrate |
|---|---|---|---|
| Lightguide end (23) | INFINITY | 0.1 | Air |
| Plano-Concave lens 1st surf. (24) | INFINITY | 2.0 | UV fused silica |
| Plano-Concave lens 2nd surf. (24) | 8.25 | 40 | Air |
| Plano-Convex lens 1st surf. (14a) | INFINITY | 6.1 | UV fused silica |
| Plano-Convex lens 2nd surf. (14a) | −51.5 | 0.5 | Air |
| Bi-Convex lens 1st surf. (14b) | 103.36 | 6.4 | UV fused silica |
| Bi-Convex lens 2nd surf. (14b) | −103.36 | — | Air |

The design of the mechanical interface of the adapter unit is conventional. The male part of the adaptor can be designed by obtaining the dimensions of the female connecting part of the microscope.

The present invention comprehends various other modifications to the above-described embodiments. For example, the sealing members may be made of glass, quartz or plastic and be of circular or polygonal cross-section, but preferably are glass rods of circular cross section. It is also envisaged that the adapter optics might additionally or alternatively employ mirrors and that only the outlet end of the lightguide might be modified to alter its optical characteristics. Also, it will be appreciated that the collector optics 14 need not comprise a plano-convex spherical is lens 14a and a bi-convex spherical lens 14b; other types of lens could be used instead. It should also be appreciated that the number of lenses need not be two.

Although the above embodiments describe the use of a lightguide to illuminate the objective field conjugate of a microscope, it will be appreciated that the system may supply light to other optical apparatus such as, for example, an apparatus for the photocuring of photosensitive products. In the latter case, the predetermined plane would be in the vicinity of the product being irradiated. Another example is a machine vision system for visual recognition in rapid manufacturing environments. In this case, the predetermined plane would be in the vicinity of the OFC of the objective lens.

Although the above-described specific embodiments use fiberbundles or liquid lightguides, the invention is applicable to other kinds of lightguides that exhibit similar non-uniformities, such as hollow aluminum light pipes.

Another means of positioning the interface 20 in close proximity to the endface 23 of the lightguide 1 is by using a sealing plug 18 that is so short that the interface 20 is close to the outlet end 5 of the guide, i.e., effectively using the end wall 18c only. However, when using such a sealing plug, it is important for the rod 18 to be of adequate length so that it can be inserted sufficiently within the sheath 16 and held securely in place. Furthermore, it is important for the sealing member to be positioned with its longitudinal axis parallel to the optical axis of the lightguide.

It should be appreciated that the approach taught by the present invention, namely displacing images of non-uniformities or imperfections away from the predetermined plane is contrary to the approach taught by U.S. Pat. No. 5,684,908 supra where no such image displacement takes place; rather such images are obviated by the use of the diffuser. Consequently, in such a system, the lens associated with the diffuser cannot have the effect of displacing images as taught by the present invention.

It should be noted that one may displace an interface or scattering centre towards or away from the OFC by translating the end face of the lightguide a slight distance away from the optimum focal position of the collector optics 14. The drawback of this is that it leads to non-optimal power coupling as well as to "under-filling" of the OFC plane to not allow for illumination of the entire plane. In the example of the microscope, if collimated light is required from the adaptor, moving the lightguide forwards or backwards will cause light to become divergent by the time it reaches the OFC and will cause vignetting of the light through the microscope's illumination optics, and hence the field of view of the microscope will be dim at the edges. This invention, at least in preferred embodiments, overcomes this disadvantage by making use of the means for displacing images of non-uniformities, which is more efficient.

Although embodiments of the invention have been described and illustrated in detail, it is to be clearly understood that the same is by way of illustration and example only and not to be taken by way of limitation, the spirit and scope of the present invention being limited only by the appended claims.

The invention claimed is:

1. Optical apparatus and a light delivery system for supplying said light to an input port of the apparatus such that the light illuminates a predetermined image plane within the apparatus, said light delivery system comprising a lightguide for conveying said light from a light source unit to said input port, the lightguide having an inlet end for connection to an output port of the light source unit and an outlet end for coupling to the input port of the apparatus so as to provide substantially uniform light at said predetermined image plane, there being imaging means at or adjacent the outlet end of the lightguide for imaging said outlet end of said lightguide at said predetermined image plane and imaging non-uniformities present at or adjacent the outlet end of the lightguide away from said predetermined image plane.

2. Optical apparatus and a light delivery system according to claim 1, wherein the imaging means comprises a lens means between the apparatus input port and said outlet end of the lightguide.

3. Optical apparatus and a light delivery system according to claim 1, wherein the imaging means comprises a lens formed as an integral part of the outlet end of the lightguide.

4. Optical apparatus and a light delivery system according to claim 2, wherein the lens is a negative lens.

5. Optical apparatus and a light delivery system according to claim 2, wherein the lens is a positive lens.

6. Optical apparatus and a light delivery system according to claim 3, wherein the lens is a negative lens.

7. Optical apparatus and a light delivery system according to claim 3, wherein the lens is a positive lens.

8. Optical apparatus and a light delivery system according to claim 1, wherein the lightguide is a liquid lightguide comprising a sheath containing a light transmissive liquid, the sheath being sealed at said inlet end and said outlet end by first and second light transmissive sealing members, respectively, there being a liquid/sealing member interface between the liquid and at least the second light transmissive member.

9. Optical apparatus and a light delivery system according to claim 8, wherein the imaging means comprises a portion of the sealing member that is configured so that the interface is positioned in relatively close proximity to the outer end face of the guide.

10. Optical apparatus and a light delivery system according to claim 9, wherein the sealing member is hollow, being closed at its outer end to form an end wall having an inner surface, the interface being at the inner surface of the end wall.

11. Optical apparatus and a light delivery system according to claim 10, wherein the sheath fits around the sealing member.

12. Optical apparatus and a light delivery system according to claim 8, further comprising a pressure gasket surrounding the external wall of the sheath adjacent the sealing member to clamp the sheath to the sealing member.

13. Optical apparatus and a light delivery system according to claim 12, wherein the pressure gasket is an O-ring.

14. Optical apparatus and a light delivery system according to claim 10, wherein the sealing member fits around the external surface of the sheath.

15. Optical apparatus and a light delivery system according to claim 8, wherein the sealing member is a glass rod.

16. Optical apparatus and a light delivery system according to claim 1, wherein the light guide comprises a fiberbundle.

17. Optical apparatus and a light delivery system according to claim 16, wherein the fiberbundle has a fused end portion and a transparent rod having one end connected to one end of the fused end portion, the distal end of the rod being the outlet end of the lightguide.

18. Optical apparatus and a light delivery system according to claim 16, wherein the imaging means comprises lens means between the apparatus input port and said outlet end of the lightguide.

19. Optical apparatus and a light delivery system according to claim 17, wherein the imaging means comprises lens means integral with said rod.

20. Optical apparatus and a light delivery system according to claim 18, wherein the lens is a negative lens.

21. Optical apparatus and a light delivery system according to claim 18, wherein the lens is a positive lens.

22. Optical apparatus and a light delivery system according to claim 1, wherein the apparatus comprises a microscope and wherein the lightguide end is placed at the focal point of a set of collector lenses such that the light that illuminates said predetermined image plane is collimated.

23. Optical apparatus and a light delivery system according to claim 1, further comprising an adapter means for coupling said outlet end of the lightguide to said input port at a predetermined position.

24. Optical apparatus and a light delivery system according to claim 23, wherein the adapter means comprises collector lens means, means for positioning the outlet end of the lightguide at a focal plane of the collector lens means at an input side thereof and means for coupling the opposite side of the collector lens means optically to the input port.

25. Optical apparatus and a light delivery system according to claim 24,
wherein the imaging means comprises a lens means between the lightguide and the collector optics.

26. A light delivery system for supplying light to an input port of an optical apparatus such that the light illuminates a predetermined image plane within the apparatus, said light delivery system comprising a light source unit for supplying said light, a lightguide for conveying said light from the light source unit to said input port; the lightguide having an inlet end connected to an output port of the light source unit and an outlet end for coupling to the input port of the apparatus so as to provide substantially uniform light at said predetermined image plane,
there being imaging means at or adjacent the outlet end of the lightguide for imaging said outlet end of said lightguide at said predetermined image plane and imaging non-uniformities present at or adjacent the outlet end of the lightguide away from said predetermined image plane.

27. A light delivery system according to claim 26, wherein the imaging means comprises a lens means.

28. A lightguide for connecting a light source unit to an optical apparatus so as to supply light to an input port of the apparatus that illuminates a predetermined image plane within the apparatus, the lightguide having an inlet end for connection to an output port of a light source unit and an outlet end for connection to the input port of the apparatus, there being means at or adjacent the outlet end of the lightguide for imaging said outlet end of said lightguide at said predetermined image plane and imaging non-uniformities present at or adjacent the outlet end of the lightguide away from said predetermined image plane.

29. A lightguide according to claim 28, wherein the imaging means comprises a lens means.

30. An adapter unit for interfacing light front a lightguide of a light delivery system to an input port of optical apparatus such that the light illuminates a predetermined image plane within the apparatus, the adaptor unit having an output port for connection to said optical apparatus and an input port for connection to the outlet end of the lightguide and comprising optical elements for providing substantially uniform light at said predetermined image plane, there being means at or adjacent the input port of the adaptor for imaging said outlet end of said lightguide at said predetermined image plane and imaging non-uniformities present at or adjacent the outlet end of the lightguide away from said predetermined image plane.

31. An adapter unit according to claim 30, wherein the imaging means comprises a lens means.

32. Optical apparatus and light delivery system according to claim 1, wherein the apparatus comprises a microscope having illumination optics and an objective and said predetermined image plane comprises an image conjugate plane of said objective,
said imaging means imaging said outlet end of said lightguide at said image conjugate plane and imaging non-uniformities present at or adjacent the outlet end of the lightguide away from said image conjugate plane.

33. Optical apparatus and light delivery system according to claim 32, wherein the imaging means comprises a negative lens.

34. Optical apparatus and light delivery system according to claim 32, wherein the imaging means comprises a positive lens.

35. Optical apparatus and light delivery system according to claim 32, wherein the imaging means comprises a negative lens.

36. Optical apparatus and light delivery system according to claim 32, wherein the imaging means comprises a positive lens.

37. A lightguide according to claim 29, wherein the lens means is integral with the outlet end of the lightguide.

38. A lightguide according to claim 29, wherein the lens means is integral with a rod at the outlet end of the lightguide.

39. Optical apparatus and a light delivery system according to claim 15, wherein the imaging means comprises lens means integral with said sealing rod.

40. Optical apparatus and a light delivery system according to claim 1, wherein the apparatus comprises a microscope and wherein the outlet end of the lightguide is so positioned relative, to a focal point of a set of collector lenses that the light that illuminates said predetermined image plane is not collimated.

* * * * *